United States Patent [19]

Baker et al.

[11] Patent Number: 5,100,619

[45] Date of Patent: Mar. 31, 1992

[54] DEVICE AND METHOD FOR COLLECTING FECAL OCCULT BLOOD SPECIMENS

[75] Inventors: Josefina T. Baker, Cupertino; David R. Shockey, San Jose, both of Calif.; Anthony DiBiase, Audubon, N.J.

[73] Assignee: Beckman Instruments, Inc., Fullerton, Calif.

[21] Appl. No.: 349,245

[22] Filed: May 9, 1989

[51] Int. Cl.$^5$ .................. G01N 33/48; G01N 33/72
[52] U.S. Cl. ........................ 422/58; 422/61; 422/56; 436/66; 436/169; 435/805
[58] Field of Search .............. 422/56, 58, 61; 436/66, 436/169; 435/299, 300, 301, 805

[56] References Cited

U.S. PATENT DOCUMENTS

| | | | |
|---|---|---|---|
| 3,996,006 | 12/1976 | Pagano | 422/50 |
| 4,092,120 | 5/1978 | Souvaniemi | 422/56 |
| 4,365,970 | 12/1982 | Lawrence | 436/66 |
| 4,420,353 | 12/1983 | Levine | 422/61 X |
| 4,427,769 | 1/1984 | Adlercreutz | 435/7.92 |
| 4,486,536 | 12/1984 | Baker | 436/66 |
| 4,645,743 | 2/1987 | Baker | 436/66 |
| 4,683,197 | 7/1987 | Gallati | 435/7.94 |
| 4,789,629 | 12/1988 | Baker et al. | 422/56 X |

FOREIGN PATENT DOCUMENTS 25983 6/1984 Australia .
10057542 8/1982 European Pat. Off. .

OTHER PUBLICATIONS

Copy of Interior and Exterior of Specimen Slide from Fuji Rebio, Inc., 1986.

Primary Examiner—Robert J. Warden
Assistant Examiner—Stephanie Blythe
Attorney, Agent, or Firm—William H. May; Gary T. Hampson; Richard P. Burgoon, Jr.

[57] ABSTRACT

A method and specimen slide for obtaining fecal occult blood specimens. The slide includes first and second portions each including front and back panels. The first portion includes one or more apertures formed through its front panel which exposes a reagent-carrying sheet and the back panel of the first portion includes a flap that may be opened for the application of additional reagents to the back of the sheet. The second portion includes an aperture in its front panel and a flap formed in its back panel. A sheet is carried between the front and back panels of the second portion onto which a fecal specimen may be smeared. The sheet includes pre-perforated removable portions that may be easily accessed through the flap. As an alternative embodiment, the back panel of the second portion may include a removable tab to which is fixed the specimen sheet. The tab and specimen sheet may be removed for easy access to the removable portions of the specimen sheet.

20 Claims, 2 Drawing Sheets

DEVICE AND METHOD FOR COLLECTING FECAL OCCULT BLOOD SPECIMENS

This application is related to co-pending patent application entitled "Specimen Collection Device and Method", Serial No. 07/349,274 filed concurrently herewith in the names of Josefina T. Baker, Robert Mervine, and Josephine T. Hucko.

FIELD OF THE INVENTION

The present invention relates to fecal occult blood testing and more particularly to a method and device suitable for obtaining multiple specimens for use in several testing techniques.

BACKGROUND OF THE INVENTION

Fecal occult blood testing has become a popular, widely used procedure to detect relatively small amounts of blood in fecal specimens. This wide use and popularity arises primarily because fecal occult blood testing is non-invasive, simple and inexpensive to perform. Because the presence of fecal occult blood in a specimen is a symptom that may be associated with colon cancer or a precursor to colon cancer, fecal occult blood testing is often routinely used on a screening basis. The routine screening of patients using fecal occult blood testing has helped to detect colon cancer at a stage where the disease is readily treatable.

A popular form of fecal occult blood testing utilizes a guaiac treated test sheet upon which a specimen of fecal material is smeared. A developing solution is applied to the opposite side of the sheet, yielding a blue color suggesting blood may be present in the fecal specimen. As the need for more specific fecal occult blood tests has been recognized, the use of immunochemical testing techniques has gained popularity. As compared to a chemical test like guaiac, an immunochemical test is more specific for the detection of human hemoglobin. However, immunochemical testing is also more complicated and expensive to perform.

Regardless of the technology used in performing the fecal occult blood test, there has been an on-going need to obtain, transport and process those specimens in a manner that is as convenient and aesthetically acceptable as possible and such that the specimen is not degraded. One form of specimen collection device that has gained wide popularity is a slide formed from folded paper or cardboard. The slide includes guaiac treated paper to which the fecal specimen is applied and a cover which is closed once the specimen application is completed. A flap in the back of the slide may be opened to reveal the back of the guaiac treated paper for subsequent application of developer and observation of the paper to determine the presence of the blue color. Examples of such a test slide are disclosed in U.S. Pat. Nos. 3,996,006 and 4,365,970.

Similar approaches have been utilized in collecting specimens for use in immunochemical tests. Typically, such tests require that a substrate such as paper to which the fecal specimen has been applied must be deposited in a vial or microtiter plate. One example of collection device is a specimen slide distributed by Fujirebio, Inc. which includes a sheet of filter paper onto which the fecal specimen is applied. The cover of the slide is closed and the slide is sent to a laboratory for analysis. To remove specimen from the device for analysis, the cover of the slide is again opened, a portion of the slide carrying the filter paper is pulled away, and a pre-punched circle is removed from the filter paper for analysis. Unfortunately, the front of the Fujirebio slide must be re-opened by the medical technologist and the technologist must grasp an area inside the slide immediately adjacent the fecal smear, thus unnecessarily exposing the medical technologist to the specimen.

With the availability of both chemical and immunochemical tests, and depending on a particular patient's symptoms and risk factors, a physician may elect to perform only one of the two tests or both of the tests. The results of the two tests can complement each other since it is known that the chemical test, such as a guaiac test, detects the heme moiety of hemoglobin while the immunochemical test detects the globin moiety of human hemoglobin. With the combined tests, the probability of detecting all of the hemoglobin moieties is greatly enhanced. Thus, a convenient specimen collection device that will facilitate one or more tests from the same specimen is desirable.

Examples of sampling devices and methods of these type are disclosed in U.S. Pat. Nos. 4,645,743 and 4,789,629. These devices, however, include a separate insert to which the fecal specimen is applied by the patient. The insert is removed from the device and the insert is then punched or sectioned to obtain a portion of the insert suitable for immunological analysis. The use of such a removable insert presents a disposal problem in addition to the device itself. Also, because the insert must be punched or sectioned, additional tools must be cleaned after each use, further complicating the process and adding expense.

SUMMARY OF THE INVENTION

The present invention overcomes the limitations and drawbacks noted above. A specimen slide in accordance with the present invention includes two inner panels and two outer panels hinged together to form a convenient folding specimen slide. One set of inner and outer panels is adapted for use with chemical testing and includes one or more apertures through which the fecal specimen may be applied to a chemically-prepared filter paper substrate. The corresponding back panel includes a flap that may be opened for the addition of developer to perform the required chemical testing. The second inner and outer panel set includes an aperture in the inner panel for applying the fecal specimen to a pre-punched specimen sheet. The back panel includes a flap to which the specimen sheet attached. Opening the flap provides ready access to the specimen sheet. In an alternative embodiment, the back panel may include a removable tab to which the specimen sheet is affixed. The tab and specimen sheet may be removed to provide easy access to the specimen coated specimen sheet and in particular to the removable portions defined by the perforations formed into the specimen sheet.

Thus, the specimen collection device of the present invention as well as the method of the present invention, provide a simple and neat means for obtaining and transporting specimens and convenient handling of the specimens for performing several forms of fecal occult blood tests.

DETAILED DESCRIPTION

Figure 1:
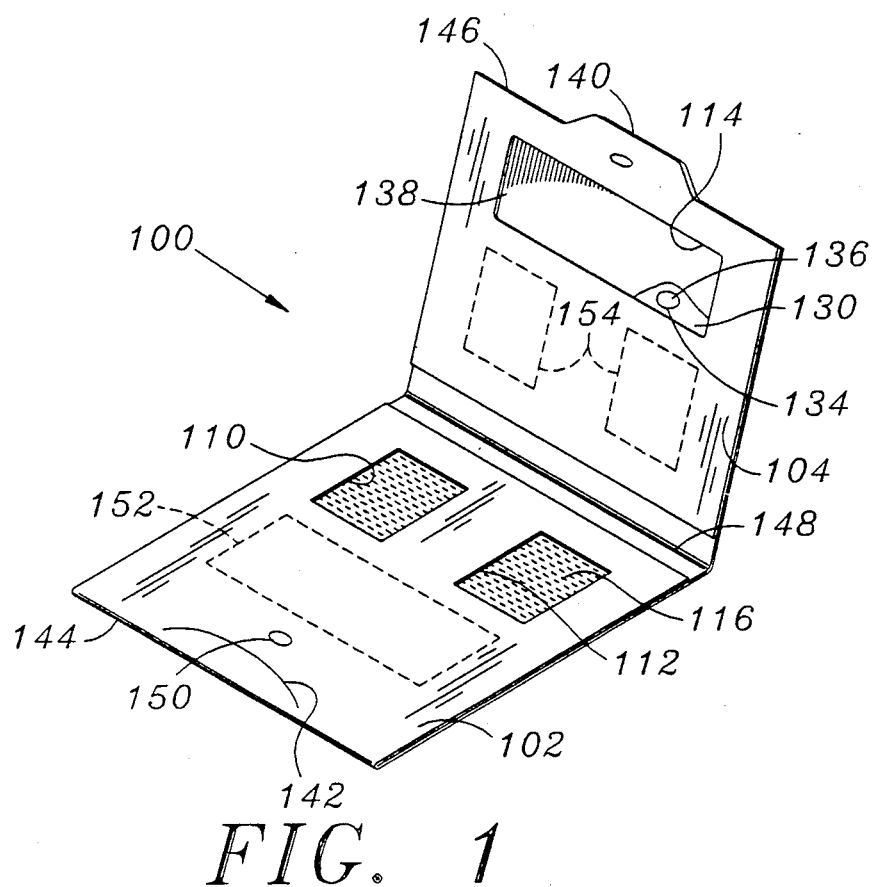
FIG. 1 is a perspective view of a combination specimen device in accordance with the present invention.
Figure 2:
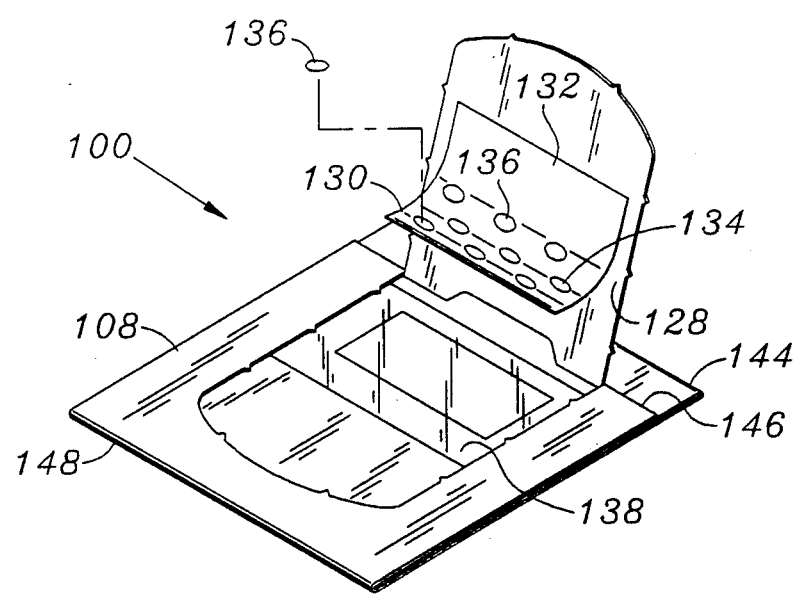
FIG. 2 is a perspective view of an outer panel of the device shown in FIG. 1.
Figure 3:
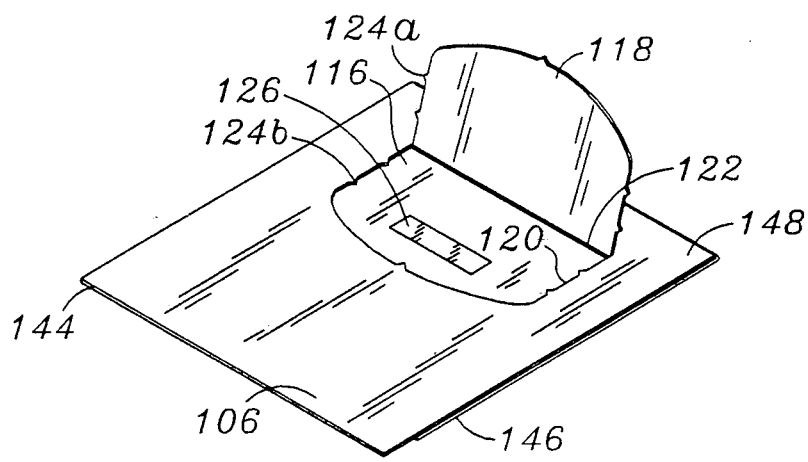
FIG. 3 is a perspective view of the other outer panel of the device shown in FIG. 1.

With reference to FIGS. 1-3, a device in accordance with the present invention is in the form of a specimen slide 100 and includes first and second inner panels 102, 104 and first and second outer panels 106, 108. The first inner panel 102 includes two apertures 110, 112 and the second inner panel 104 includes a larger rectangular aperture 114. A sheet 116 of absorbent material is fixed between the first inner panel 102 and first outer panel 106. In the embodiment disclosed herein, the sheet 116 is filter paper which carries a reagent that will react with hemoglobin components from blood and a peroxide solution to form a visible colored compound. Such a reagent may be guaiac, tetramethyl benzidine, ortho tolidine, and other similar chromogens. In the embodiment disclosed herein, the reagent carried by the sheet 116 is guaiac.

A flap 118 (shown in its open position in FIG. 3) is defined in the first outer panel 106 by an outline of perforations 120 and a crease 122 which serves as a hinge. The perforations 120 are spaced to define a plurality of bridges 124, each comprising bridge portions 124a, 124b between the flap 118 and the surrounding portion of the first outer panel 106. The bridges 124 hold the flap 118 in place until the bridges 124 are broken as the flap 118 is opened along the crease line 122 to reveal the back side of the reagent carrying filter paper 116. An area defining monitors suitable for indicating the performance of the guaiac carrying filter paper 116 and reagents which may be applied thereto is indicated at 126 and may be of the form described, for example, in U.S. Pat. No. 4,365,970.

A flap 128 is formed into the second outer panel 108 and is defined by an outline of bridged perforations as with the flap 118 which hold the flap 128 in its initial closed position (not shown).

A specimen sheet 130 formed, for example, from filter paper, is fixed at one edge 132 to the inner surface of the flap 128 and includes a plurality of perforations 134 which in turn define a plurality of removable portions 136. A thin sheet of mesh or porous screening material 138 (shown partially cut-away in FIG. 1) is fixed between the second inner and outer panels 104, 108 and appears through the aperture 114. With the flap 128 in the initial closed position, the specimen sheet 130 is pressed against the screening material 138. The screening material 138 is a high strength, high porosity tissue composed, for example, of cellulosic fiber or synthetic materials, such as polyester or nylon mesh. Suitable materials include "Hollytex" brand material, grade 3257, from Eaton-Dikeman Division of Filtration Sciences Corporation, Mount Holly Springs, Pa., and grade 785 tissue from the C. H. Dexter Division of The Dexter Corporation, Windsor Locks, Conn.

The specimen slide 100 is preferably formed from a single sheet or panel of paper or cardboard. The cardboard is die-cut to form the apertures 110, 112 and 114 as well as the perforations to define the flaps 118 and 128. A tab 140 is also formed at the outer edge of the second inner and outer panels 104, 108. The tab 140 is adapted to engage a semi-circular slit 142 formed near an outer edge 144 of the first inner and outer panels 102, 106. The slit 142 is also formed by, for example, die-cutting during the manufacturing process of the slide 100.

In a preferred embodiment as disclosed herein, the specimen sheet 130 is cut from a length of filter paper prepared with a repeating pattern of perforations 134. The repeating pattern allows the specimen sheet 130 to be positioned on the flap 128 without precise alignment of the removable portions 136 with respect to the aperture 114. In the embodiment disclosed herein, about nine removable portions 136 are carried by the specimen sheet 130 cut from the length of prepared filter paper, although other arrangements of removable portions 136 would also prove suitable.

The filter paper 116, specimen sheet 130 and screening material 138 are positioned and fixed by a suitable adhesive or glue. The first inner and outer panels 102, 106 are folded along the edge 144 and are pressed and held together by means of a suitable glue or adhesive. Similarly, the second inner and outer panels 104, 108 are folded to define edge 146 and the panels are pressed and held together by means of a suitable glue or adhesive. The slide 100 is folded along a hinge 148 defined between the outer panels 106, 108. A drop of glue 150 holds the first and second inner panels 102, 104 together until the slide 100 is ready for use. With the slide 100 closed, the aperture 114 is proximate the first inner panel 102 as shown with outline 152 and the apertures 110, 112 are proximate the second inner panel 104 as shown with outlines 154.

Figure 4:
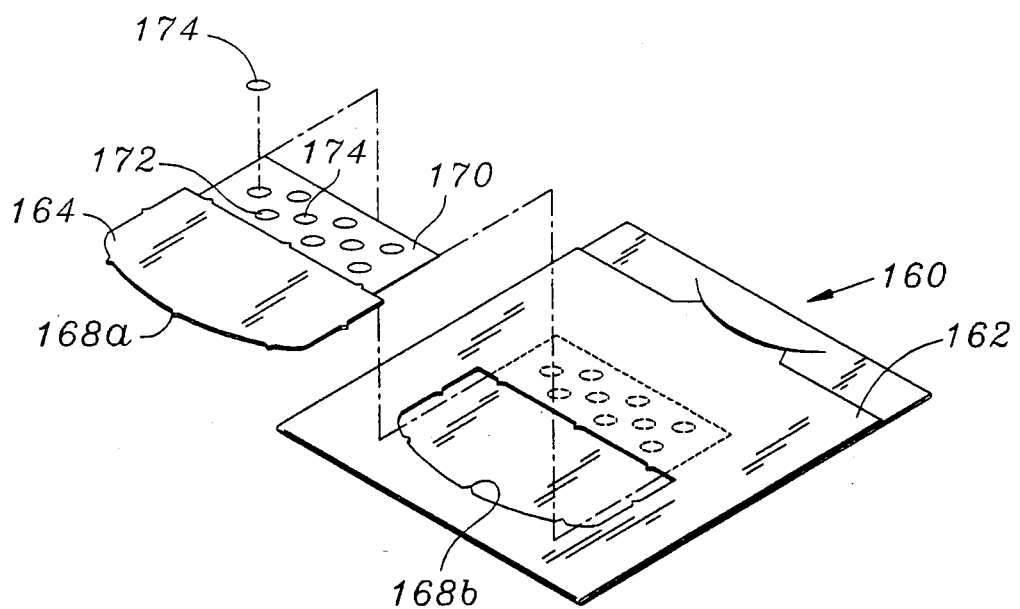
FIG. 4 is a perspective view of an alternative embodiment of the back panel illustrated in FIG. 2.

In an alternative embodiment of the present invention shown in FIG. 4, the specimen slide 160 is essentially identical to the specimen slide 100 and includes an outer panel 162 corresponding to the first outer panel 108 of the specimen slide 100. The outer panel 162 is die-cut to form spaced perforations which define a pull-out tab 164. The tab 164 is removably held in place with the remainder of the outer panel 162 by bridges 168, each comprising bridge portions 168a, 168b. A specimen sheet 170 is affixed to the tab 164 and includes a plurality of perforations 172 which define corresponding circular removable portions 174.

With the tab 164 positioned as a part of the outer panel 162, the specimen sheet 170 is positioned identically to the specimen sheet 130 when the flap 128 of the slide 100 is closed. The specimen sheet 170 when so positioned is within the specimen slide 160 is as shown in phantom outline in FIG. 4.

In using the specimen slide 100, fecal specimens are smeared onto the filter paper 116 through the apertures 110 and 112. The fecal specimen is also applied through the aperture 114 and screening material 138 to the specimen sheet 130. The patient closes the specimen slide 100 by folding along the edge 146 and inserting the tab 140 beneath the slit 142. The specimen slide 100 is transported to the physician's office or laboratory for analysis.

The analysis of the fecal specimens carried by the specimen slide 100 may be carried out advantageously without reopening the specimen slide 100 to gain access to the inner panels 102, 104. The flap 118 is opened and a developer solution is applied to the back of the filter paper 116 and the area 126 to perform a screening test for occult blood in the specimen.

If the results of the guaiac test performed on the filter paper 116 indicate that an immunochemical test of the specimen is appropriate, or if the physician had ordered both the guaiac test as well as a second test such as an immunochemical test, the flap 128 is opened, revealing the specimen sheet 130. The loose edge of the specimen sheet 130 may be lifted and one or more of the removable portions 136 to which specimen has been applied may be readily removed for the further testing and analysis.

In the alternate embodiment illustrated in FIG. 4, the pull-out tab 164 is freed from the outer panel 162 and is withdrawn to reveal the specimen sheet 170. One or more of the removable portions 174 to which specimen has been applied may be then easily removed for further testing and analysis.

Other modifications to the present invention will be readily apparent to those skilled in the art. For example, the specimen slide 100 or 160 may be constructed without the screening material 138. Also the shapes and sizes of the apertures 110, 112 and 114 may vary according to, for example, the size and shape of the specimen slide or the amount of specimen that is to be applied to the specimen sheet. For example, a smaller aperture may have the effect of concentrating the specimen in a smaller area, improving the reproducibility of the specimen gathering technique. The size and shape of the removable portions 136, 174 may be varied to carry more or less specimen to thereby accommodate differing sensitivities of testing methodologies.

Furthermore, sheet 116 may be sensitized for other analytes and the device may be adapted for collecting other types of specimens, such as blood from finger pricks or material collected using swabs. Also, an alternative device may not include the sheet 116 and instead may include a simple cover such as the cover 8 disclosed in U.S. Pat. No. 3,996,006 which is incorporated by reference, in place of the first inner and outer panels 102, 106. Such a device thus serves as a specimen collection device only. In such an instance, either the embodiment of the specimen sheet 130 or the specimen sheet 170 may be used.

Advantageously, the specimen slides 100 and 160 allow access to the fecal specimens without reopening the slide itself. Furthermore, the specimen slide 100 does not yield any additional sub-parts or components which may require separate disposal. Both of the specimen slides 100 and 160 provide a convenient and aesthetically improved means for collecting fecal specimens for analysis and improved handling of the specimens for a combination chemical and immunochemical testing sequence.

The present invention is not to be limited to the detailed description contained herein but is to be afforded the full scope of the appended claims and all equivalents thereto.

We claim:

1. A specimen slide, comprising:
   a first portion having a first front panel and a first back panel;
   a second portion having a second front panel and a second back panel, the first and second portions joined by hinge means for folding the first and second portions together;
   an aperture in the first front panel;
   a first sheet fixed between the first front and back panels and positioned for receiving a fecal specimen through the aperture, the sheet carrying a reagent;
   the second front panel including an aperture positioned in the second front panel such that the aperture does not align with the aperture in the first front panel;
   a second sheet between the second front and back panels, the sheet including perforations defining at least one removable portion of the sheet appearing through the aperture;
   means for removable securing the first portion and the second portion in a closed position with the first and second front panel facing one another;
   flap means in the first back panel opposite the aperture for providing access to a second side of the first sheet; and
   access means in the second rear panel for exposing a second side of the second sheet for removal of the at least one removable portion.

2. A specimen slide as in claim 1 wherein the access means comprises a hinged flap and a portion of the second sheet is movable with the flap.

3. A specimen slide as in claim 1 wherein the access means comprising a removable tab and the second sheet is removable with the tab.

4. A specimen slide as in claim 1 wherein the slide further includes screen means between the aperture in the second front panel and the second sheet for blocking excessive specimen from being applied to the second sheet.

5. A specimen slide as in claim 4 wherein the second sheet includes a plurality of removable portions defining at least in part a repeating pattern.

6. A specimen slide as in claim 5 wherein the second sheet is sectioned from a length of material having a repeating pattern of the removable portions.

7. A method for obtaining a specimen suitable for use in testing using a specimen slide including first and second portions joined by hinge means for folding the first and second portions together, the first portion including a first front panel and a first back panel, an aperture in the first front panel, an openable flap in the first back panel, and a reagent-carrying sheet carried between the front and back panels, the second portion including second front and back panels, an aperture in the second front panel, an openable flap in the second back panel, and a specimen sheet carried between the second front and back panels, the specimen sheet including removable portions, the method comprising the steps of:
   (a) obtaining a specimen;
   (b) smearing a portion of the specimen on the reagent-carrying sheet through the aperture in the first front panel;
   (c) smearing a portion of the specimen onto the specimen sheet through the aperture in the second front panel;
   (d) closing the specimen slide such that the first and second front panels are facing one another;
   (e) opening the flap in the first back panel;
   (f) applying another reagent to the back of the reagent-carrying sheet;
   (g) selectively opening the flap in the second back panel, removing the removable portion and performing a second test using the removable portion.

8. A method as in claim 7 wherein the specimen sheet is fixed to and movable with the flap and the second back panel and step (g) further includes opening the flap and lifting a portion of the specimen sheet away from the flap to assist in the removal of the removable portion.

9. A method as in claim 7 wherein the flap in the second back panel is removable and the specimen sheet is removable with the flap, the method of step (g) further including the step of removing the flap and the specimen sheet for providing access to the removable portion.

10. A method as in claim 7 wherein the slide includes screen means between the aperture in the first front panel and the specimen receiving sheet and step (c) further includes applying the specimen through the screen means for blocking excessive specimen from being applied to the specimen sheet.

11. A method of forming a slide of claim 7 including the steps of forming a length of material having a repeating pattern of perforations defining a plurality of removable portions and cutting a portion of the length of material to form the second sheet.

12. A method as in claim 7 wherein the step of obtaining a specimen includes obtaining a fecal specimen.

13. A specimen slide, comprising:
a front panel and a back panel, the front panel including an aperture;
a closeable cover hinged to the front panel;
a sheet between the front and back panels, the sheet including perforations defining at least one removable portion of the sheet appearing through the aperture;
flap means in the back panel opposite the aperture for providing access to a second side of the sheet;
a hinged flap in the rear panel and a portion of the sheet is movable with the flap.

14. A specimen slide, comprising:
a front panel and a back panel, the front panel including an aperture;
a sheet between the front and back panels, the sheet including perforations defining at least one removable portion of the sheet appearing through the aperture;
flap means in the back panel opposite the aperture for providing access to a second side of the sheet; and
a removable tab formed in the rear panel and the sheet is removable with the tab.

15. A specimen slide as in claim 13 wherein the slide further includes screen means between the aperture and the sheet for blocking excessive specimen from being applied to the sheet.

16. A specimen slide as in claim 14 wherein the slide further includes screen means between the aperture and the sheet for blocking excessive specimen from being applied to the sheet.

17. A specimen slide as in claim 13 wherein the sheet includes a plurality of removable portions defining at least in part a repeating pattern.

18. A specimen slide as in claim 17 wherein the sheet is sectioned from a length of material having a repeating pattern of the removable portions.

19. A specimen slide as in claim 14 wherein the sheet includes a plurality of removable portions defining at least in part a repeating pattern.

20. A slide as in claim 19 wherein the sheet is sectioned from a length of material having a repeating pattern of the removable portions.

* * * * *